(12) United States Patent
Collery et al.

(10) Patent No.: US 8,987,491 B2
(45) Date of Patent: Mar. 24, 2015

(54) RHENIUM COMPLEXES AND THEIR PHARMACEUTICAL USE

(75) Inventors: Philippe Collery, Bastia (FR); Jean D'Angelo, Massy (FR); Georges Morgant, Le Kremlin-Bicetre (FR)

(73) Assignees: Societe de Coordination de Recherches Therapeutiques, Algajola (FR); Universite Paris-Sud 11, Orsay (FR); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 13/701,191

(22) PCT Filed: Jun. 1, 2011

(86) PCT No.: PCT/EP2011/059113
§ 371 (c)(1),
(2), (4) Date: Feb. 15, 2013

(87) PCT Pub. No.: WO2011/151399
PCT Pub. Date: Dec. 8, 2011

(65) Prior Publication Data
US 2013/0158109 A1   Jun. 20, 2013

(30) Foreign Application Priority Data
Jun. 1, 2010 (EP) .................................. 10305578

(51) Int. Cl.
| | | |
|---|---|---|
| C07F 17/00 | (2006.01) | |
| A61K 31/28 | (2006.01) | |
| A61K 33/24 | (2006.01) | |
| A61K 45/06 | (2006.01) | |
| C07F 13/00 | (2006.01) | |

(52) U.S. Cl.
CPC ............... *A61K 31/28* (2013.01); *A61K 33/24* (2013.01); *A61K 45/06* (2013.01); *C07F 13/005* (2013.01); *C07F 13/00* (2013.01)
USPC ........................................... 556/46; 514/492

(58) Field of Classification Search
USPC ........................................... 556/46; 514/492
See application file for complete search history.

(56) References Cited

U.S. PATENT DOCUMENTS

| | | | |
|---|---|---|---|
| 2,602,816 A | 7/1952 | Gregory et al. | |
| 2,657,231 A | 10/1953 | Klarer et al. | |
| 3,217,004 A | 11/1965 | Hechenbleikner et al. | |
| 3,769,436 A | 10/1973 | Lafon | |
| 6,573,293 B2 | 6/2003 | Tang et al. | |
| 2007/0071672 A1 | 3/2007 | Alberto et al. | |

FOREIGN PATENT DOCUMENTS

| | | |
|---|---|---|
| GB | 1307227 | 2/1973 |
| JP | 3-091735 | 4/1991 |
| WO | WO 2005/039648 | 5/2005 |

OTHER PUBLICATIONS

Kermagoret. A., et al. Polyhedron vol. 30, pp. 347-353. Published online Nov. 9, 2010.*
FDA Approved Solvents List. Published Nov. 2003.*
Liaw, W-F et al., Journal of the Chinese Chemical Society vol. 42, pp. 59-65, Published 1995. Abstract Provided.*
Berger, R. et al., Wissenschaftlich-Technische Berichte-Forschungszentrum Rossendorf, vol. FZR-270, pp. 202-209 Published 1999. Abstract provided.*

(Continued)

*Primary Examiner* — Paul Zarek
*Assistant Examiner* — George W Kosturko
(74) *Attorney, Agent, or Firm* — Hamre, Schumann, Mueller & Larson, P.C.

(57) ABSTRACT

The present invention is directed to a rhenium complex of general Formula (I) or a pharmaceutically acceptable salt or solvate thereof, wherein X is Se; Y is NH, O or S or is a methylene group; Z is halogen; m=0, 1, or 2 and p=0, 1, or 2, provided that m and p are both different from zero when Y is NH, O or S; n=3; R' is a phenyl group or a group of general Formula —$(CH_2)_q$—COOH wherein q=1 or 2, a pharmaceutical composition comprising a therapeutically effective amount of at least one of such rhenium complex where X is additionally S or Te, a method for preparing said rhenium complex and a method for treating a proliferative growth related-disorder using a therapeutically effective amount of at least one of said rhenium complex where X is additionally S or Te. Also claimed is the use of compounds of formula (II) in the preparation of compounds of formula (I).

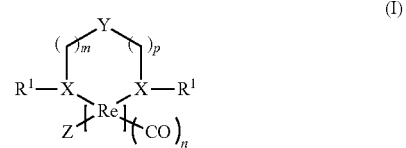

(I)

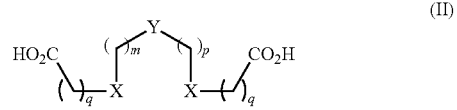

(II)

10 Claims, 2 Drawing Sheets

(56) References Cited

OTHER PUBLICATIONS

Liaw et al.: "Rhenium(I) Tellurolate, Telluroether and Bidentate-Telluroether Complexes: Crystal Structures of $Re(CO)_3Br(PhTe(CH_2)_3TePh)$, $PhTeRe(Co)_5$, $Re_2(\mu\text{-}SePh)_2(CO)_8$ and $[(PhTeMe)Re(CO)_5][BF_4]$"; Journal of the Chinese Chemical Society, vol. 42, No. 1, 1995, pp. 59-65. XP009140921.

Berger et al.: "Miscellaneous Results of Determining the Partition Coefficients and Ionization Constants for Rhenium and Technetium Coordination Compounds by Using HPLC"; Berichte Forschungszentrum Rossendorf, vol. FZR-270, 1999, pp. 202-209, XP001525544.

Pietzsch et al.: "Chemical and Biological Characterization of Technetium(I) and Rhenium(I) Tricarbonyl Complexes with Dithioether Ligands Serving as Linkers for Coupling the $Tc(CO)_3$ and $Re(CO)_3$ Moieties to Biologically Active Molecules", Bioconjugate Chemistry, vol. 11, No. 3, May 15, 2000, pp. 414-424, XP001119310.

Pietzsch et al.: "Rhenium and Technetium Carbonyl Complexes for the Labelling of Bioactive Molecules or Small Peptides. Part1. Preliminary Investigations on the Comlex Formation of the Tetradentate Thioether $HOOC\text{-}CH_2\text{-}S\text{-}CH_2CH_2\text{-}S\text{-}CH_2\text{-}COOH$ with $[ReBr_3(CO)_3]$", Berichte Forschungszentrum Rossendorf, vol. FZR-122, 1996, pp. 114-116, XP001525543.

Holmberg: Organische Polysulfide-Organic Polysulphides; Justus Liebigs Annalen Der Chemie, vol. 359, 1908, pp. 81-99, XP009026532.

Addison et al.: "Synthesis of Some Benzimidazole- and Benzothiazole-Derived Ligand Systems and Their Precursory Diacids"; Journal of Heterocyclic Chemistry, vol. 20, No. 6, Nov. 1983, pp. 1481-1484, XP001083993.

Baliah et al.: "Synthesis of 5-Aryl-4,6-bis[alkoxycarbonyl]-1,3-dithiane 1,1,3,3-Tetroxides" Synthesis, Dec. 1981, pp. 995-996, XP007915763.

Fredga: "Eine Methode zur Darstellung von Carbonsäuren organischer Selenide"; Chemisches Zentralblatt, vol. 107, 1936, pp. 1704-1705, XP009141176.

Casassas et al.: "Complexes métalliques du bis[2-[(carboxyméthyl)thio]éthyl] éther", Journal De Chimie Physique, vol. 74, No. 4, 1977, pp. 424-426, XP009141183.

Larsson et al.: Several new polymethylene (bis-beta-mercapto acids), Chalmers Tekniska Högskolas Handlingar—Transactions of Chalmers University of Technology Gothenburg, vol. 47, 1945, pp. 13-14, XP009141192.

Labuk et al.: "Reaction of Elemental Sulfur with Acrylonitrile. Synthesis of 1,7-Dicyano-3,4,5-Trithiaheptane"; Phosphorus, Sulfur, and Silicon and the Related Elements, vol. 42, No. 1&2, 1989, pp. 107-109, XP009141191.

Voronkov et al.: "Photochemical Reactions of Ethynylsilanes with 2-Mercaptoethanol and Mercaptoacetic Acid"; Journal of General Chemistry of the USSR, vol. 58, No. 8, 1988, pp. 1631-1633, SP009141236.

Shtemenko et al.: "Synthesis, characterization, in vivo antitumor properties of the cluster rhenium compound with GABA ligands and its synergism with cisplatin"; Dalton Trans., The Royal Society of Chemistry, 2009, pp. 5132-5136.

Picón-Ferrer et al.: "Chloro-*fac*-tricarbonylrhenium(I) complexes of asymmetric azines derived from 6-acetyl-1,3,7-yrimethylpteridine-2,4(1H,3H)-dione with hydrazine and aromatic aldehydes: Preparation, structural characterization and biological activity against several human tumor cell lines", Journal of Inorganic Biochemistry 103 (2009), pp. 94-100.

Orsa et al.: "The one-pot synthesis and the fluorescence and cytotoxicity studies of chlorotricarbonyl($\alpha$-diimine)rhenium(I),*fac*-$(CO)_3(\alpha\text{-diimine})ReCl$, Complexes"; Inorganic Chemistry Communications 11 (2008), pp. 1054-1056.

Zhang et al.: "Tricarbonylrhenium(I) complexes of phosphine-derivatized amines, amino acides and a model peptide: structures, solution behavior and cytotoxicity"; Journal of Organometallic Chemistry 650, (2002), pp. 123-132.

Wang et al.: "Synthesis, X-ray structures, and cytotoxicity of rhenium(I) carbonyl 2-(dimethylamino) ethoxide complexes"; Polyhedron 21 (2002), pp. 1991-1999.

Guilliver et al.: "Synthesis, Properties, and Multinuclear ($^1H$, $^{13}C$, $^{77}Se$) Nuclear Magnetic Resonance Studies of Selenoethers containing Two or More Selenium Atoms"; J. Chem. Soc. Perkin Trans. II (1984), pp. 429-434.

Pitombo et al.: "A Novel Synthesis of 1,2-Diselenolethane Derivatives"; Rev. Latinoam. Quim. 12 (1982), pp. 108-109.

Illán-Cabeza et al.: "Synthesis, characterization and antiproliferative behavior of tricabonyl complexes of rhenium(I) with some 6-amino-5-nitrosouracil derivatives: Crystal structure of *fac*-$[ReCl(CO)_3(DANU\text{-}N^5,O^4)]$ (DANU=6-amino-1,3-dimethyl-5-nitrosouracil)"; Journal of Inorganic Biochemistory 99 (2005), pp. 1637-1645.

Ma et al.: "DNA Binding and Cytotoxicity of Ruthenium(II) and Rhenium(I) Complexes of 2-Amino-4-phenylamino-6-(2-pyridyl)-1,3,5-triazine"; Inorganic Chemistry, vol. 46, No. 3 (2007), pp. 740-749.

Elwell et al.: "A fluorine containing bipyridine cisplatin analog is more effective than cisplatin at inducing apoptosis in cancer cell lines"; Bioorganic & Medicinal Chemistry 14 (2006), pp. 8692-8700.

Abel et al.: "Conformational Studies of Dithiastannolanes by Dynamic Nuclear Magnetic Resonance Spectroscopy"; J. Chem. Soc., Dalton Trans. (1982), pp. 2065-2072.

Greene et al.: "Protective Groups in Organic Synthesis"; 3rd Edition, John Wiley & Sons, 1999.

Liang et al.: "Fast-dissolving intraoral drug delivery systems"; Expert Opinion, Therapeutic Patents (2011) 11(6), pp. 981-986.

Altomare et al.: "Computer Programs, SIR97: a new tool for crystal structure determination and refinement"; J. Appl. Crystallogr. 32 (1999), pp. 115-119.

\* cited by examiner (a)

(b)

RHENIUM COMPLEXES AND THEIR PHARMACEUTICAL USE

BACKGROUND

The present invention relates to stable rhenium complexes which may be useful in the treatment of certain tumours.

Cisplatin and some platinum-based related drugs are known to be useful in the treatment of a variety of neoplastic diseases.

However, the clinical success of these drugs is limited by significant side effects, due in part, to the inherent toxicity of the platinum element (particularly, its nephrotoxicity).

In this respect, other transition metals have been contemplated for their use in pharmaceutical applications and rhenium (Re) has been postulated to be one of the least toxic.

Accordingly, rhenium-based compounds such as dirhenium clusters described in A. V. Shtemenko et al., Dalton Trans. (2009) 5132-5136 and azine-based rhenium complexes such as the ones described in I. Picón-Ferrer et al., J. Inorg. Biochem. 103 (2009) 94-100 have already been targeted as potential anti-tumour candidates which may be suitable to enter clinical development.

Several types of ligands for the rhenium metal are known. More particularly, a number of bidentate ligands have been described to form stable complexes with a single rhenium atom and show a propensity to cytotoxicity against various tumour cell lines.

Amongst these bidentate ligands it can be cited diimine ligands such as the ones depicted in D. K. Orsa et al., Inorg. Chem. Comm. 11 (2008) 1054-1056, diphenylphosphine ligands such as the ones described in J. Zhang et al., J. Organomet. Chem. 650 (2002) 123-132 or for example 2-(dimethylamino)ethoxide complexes proposed by Wenwu Wang et al. in Polyhedron 21 (2002) 1991-1999.

SUMMARY

One aspect of the present disclosure relates to a rhenium complex having the structure of Formula (I),

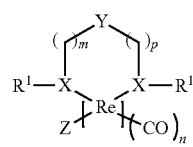

(I)

or a pharmaceutically acceptable salt or solvate thereof, wherein:
X is chosen from S, Se or Te;
Y is NH, O or S or is a methylene group;
Z is halogen;
m=0, 1, or 2 and p=0, 1, or 2, provided that m and p are both different from zero when Y is NH, O or S;
n=3;
$R^1$ is a phenyl group or a group of general Formula $-(CH_2)_q-COOH$ wherein q=1 or 2.

Certain other aspects of the disclosure relate to specific embodiments of compounds of Formula (I) wherein X is a selenium atom (Se).

In humans, selenium is a trace element nutrient which, amongst other things, functions as cofactor for reduction of antioxidant enzymes such as glutathione peroxidases. Accordingly, the use of selenium in combination with a rhenium complex may be advantageous in therapeutic applications such as assisting in the improvement of the cytotoxic effect of the resulting metal complex against tumour cells.

Certain other aspects of the disclosure relate to a rhenium complex of general Formula (I) wherein $R^1$ is a group of general Formula $-(CH_2)_q-COOH$, q being equal to 1 or 2.

Certain other aspects of the disclosure relate to specific embodiments of compounds of Formula (I) wherein m=p=1 and Y is chosen from a methylene group ($CH_2$) or a NH group, or alternatively, wherein one of m or p is taken to be equal to zero and the other is 1 whilst Y is a methylene group ($CH_2$).

Further aspects of the disclosure relate to specific embodiments of compounds of Formula (I) wherein the rhenium complex of general Formula (I) is more specifically a complex of general Formula (Ia):

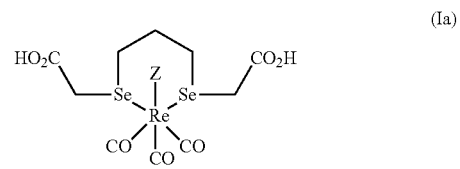

(Ia)

or a complex of general Formula (Ib),

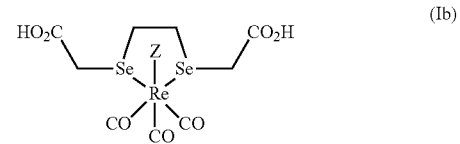

(Ib)

or pharmaceutically acceptable salts or solvates thereof, wherein Z is chosen from chlorine (Cl) or bromine (Br), preferably chlorine.

Further aspects of the present disclosure relate to a pharmaceutical composition comprising a therapeutically effective amount of at least one rhenium complex of general Formula (I), or a pharmaceutically acceptable salt or pro-drug thereof or a hydrate or solvate of such complex, either alone or in combination with a second agent, and a pharmaceutically acceptable carrier, vehicle, diluent or excipient.

The pharmaceutical composition of the invention may comprise one or more other active agents, in which case the compound of Formula (I) and the other agent(s) may be administered as part of the same or separate dosage forms, via the same or different routes of administration, and on the same or different administration schedules according to standard pharmaceutical practice.

Additional aspects of the present disclosure relate to a compound of general Formula (II),

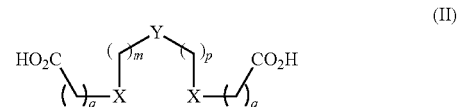

(II)

or a pharmaceutically acceptable salt or solvate thereof, herein X, Y, m, p and q are as defined above.

Compounds of general Formula (II) may be used as ligands of a transition metal such as rhenium to form a complex of general Formula (I) which is suitable to solve the technical problem underlying the present invention.

Still other aspects of the present disclosure relate to a use of a compound of general Formula (II) or a pharmaceutically acceptable salt or solvate thereof, wherein X, Y, m, p and q are as defined above for the preparation of a compound of formula (I), preferably via a method for preparing rhenium complexes of general Formula (I) comprising the step of reacting a compound of Formula (II) with $Re(CO)_5Cl$. The reaction can be carried out in a suitable solvent such as THF or methylene chloride.

Additional aspects of the present disclosure relate to a rhenium complex of general Formula (I) for use in a method for treating a proliferative growth related-disorder in mammals, including humans.

The rhenium complex of general Formula (I) or a pharmaceutically acceptable salt or solvate thereof may also be used for the preparation of a medicament for treating a proliferative growth related-disorder in mammals, including humans.

More specifically, proliferative growth related-disorders in which the present rhenium complex is useful include a variety of cancers, including (but not limited to) the following:

carcinoma, including that of the prostate, pancreatic ductal adeno-carcinoma, breast, colon, lung, ovary, pancreas, and thyroid;

tumors of the central and peripheral nervous system, including neuroblastoma, glioblastoma, and medulloblastoma; and other tumors, including melanoma and multiple myeloma.

Even more specifically, the rhenium complex of general Formula (I) is useful in the treatment of solid tumours and preferably breast tumours.

More specifically, proliferative growth related-disorders in which the present rhenium complex is useful include (but not limited to) hematopoietic malignant diseases, viral cellular proliferations, auto-immune diseases and immune system diseases.

Further aspects of the present disclosure relate to a method of treating a proliferative growth related-disorder comprising administering to said mammal in need of such treatment a therapeutically effective amount of at least one rhenium complex of general Formula (I) or a pharmaceutically acceptable salt, pro-drug or hydrate or solvate of such complex, either alone or in combination with a second agent, and a pharmaceutically acceptable carrier, vehicle, diluent or excipient.

In one embodiment, the invention relates to a compound of Formula (I) selected from any one of the compounds exemplified hereinbelow, or pharmaceutically acceptable salts, hydrates, solvates or pro-drugs thereof.

In another embodiment, the invention relates to a compound of Formula (I) selected from the group consisting of:
[Chloro(1,4-diphenyl-1,4-dithiabutane-S,S)tricarbonylrhenium(I)],
[Chloro(1,5-diphenyl-1,5-dithiapentane-S,S)tricarbonylrhenium(I)],
[Chloro(1,6-dicarboxy-2,5-dithiahexane-S,S)tricarbonylrhenium(I)],
[Chloro(1,7-dicarboxy-2,6-dithiaheptane-S,S)tricarbonylrhenium(I)], and
pharmaceutically acceptable salts or solvates of said compounds.

DEFINITIONS

As used herein, the phrase "bidentate ligand" generally refers to a chelating agent having two groups capable of attachment to a metal ion.

As used herein, the phrase "solid tumour" generally refers to an abnormal mass of tissue that usually does not contain cysts or liquid areas. Solid tumours may be benign (not cancer), or malignant (cancer). Different types of solid tumours are named for the type of cells that form them. Examples of solid tumours are sarcomas, carcinomas, and lymphomas. Leukemia tumours generally do not form solid tumours.

As used herein, the phrase "pharmaceutically acceptable" indicates that the designated carrier, vehicle, diluent, excipient, salt or prodrug is generally chemically and/or physically compatible with the other ingredients comprising a formulation, and is physiologically compatible with the recipient thereof.

The terms "treating", "treated", and "treatment" as used herein include preventative (e.g., prophylactic), ameliorative, palliative and curative uses and/or results.

The phrases "therapeutic" and "therapeutically effective amount" as used herein denote an amount of a compound, composition or medicament that (a) treats or prevents a particular disease, condition or disorder; (b) attenuates, ameliorates or eliminates one or more symptoms of a particular disease, condition or disorder; (c) prevents or delays the onset of one or more symptoms of a particular disease, condition or disorder described herein. It should be understood that the terms "therapeutic" and "therapeutically effective" encompass any one of the aforementioned effects (a)-(c), either alone or in combination with any of the others (a)-(c).

Certain compounds of the present invention may occur as mixtures of enantiomers and as individual (pure) enantiomers, as well as diastereomers and mixtures of different diastereomers. The present invention includes all such enantiomers and diastereomers and mixtures thereof in all ratios.

In addition, the scope of the present invention includes all stereoisomers, as well as all geometric isomers and tautomeric forms (tautomers) of the compounds of Formula (I), and all mixtures thereof in any ratio. It will be appreciated by one skilled in the art that a single compound may exhibit more than one type of isomerism.

Compounds of the present invention may be resolved into the pure enantiomers by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support with a bound chiral ligand or in the presence of a chiral solvent. It will be appreciated that where the desired stereoisomer is converted into another chemical entity by one of the separation procedures described above, a further step is required to liberate the desired enantiomeric form. Alternatively, the specific stereoisomers may be synthesized by using an optically active starting material, by asymmetric synthesis using optically active reagents, substrates, catalysts or solvents, or by converting one stereoisomer into the other by asymmetric transformation or inversion.

Wherein said compounds of the present invention contain one or more additional stereogenic centers, those skilled in the art will appreciate that all diastereoisomers and diastereoisomeric mixtures of the compounds illustrated and discussed herein are within the scope of the present invention. These diastereoisomers may be isolated by methods known to those skilled in the art, for example, by crystallization, gas-liquid or liquid chromatography.

Alternatively, intermediates in the course of the synthesis may exist as racemic mixtures and be subjected to resolution by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support with a bound chiral ligand or in the presence of a chiral solvent. It will be appreciated that where the desired stereoisomer is converted into another chemical entity by one of the separation procedures described above, a further step is required to liberate the desired enantiomeric form. Alternatively, specific stereoisomers may be synthesized by asymmetric synthesis using optically active reagents, substrates, catalysts or solvents, or by converting one stereoisomer into the other by asymmetric transformation or inversion.

The compounds of the present invention may exist in unsolvated as well as solvated forms with pharmaceutically acceptable solvents such as water, ethanol, and the like. It should be understood that pharmaceutically acceptable solvents includes isotopically substituted solvents such as $D_2O$, $d^6$-DMSO and the like. The term 'solvate' is used herein to describe a complex comprising the compound of the invention and one or more pharmaceutically acceptable solvent molecules. It is intended that the present invention embrace unsolvated forms, solvated forms and mixtures of solvated forms.

Certain compounds of the present invention and/or their salts and/or solvates may exist in more than one crystal form. Polymorphs of compounds represented by Formula I are encompassed in the present invention and may be prepared by crystallization of a compound of Formula I under different conditions such as, for example, using different solvents or different solvent mixtures; crystallization at different temperatures; various modes of cooling ranging from very fast to very slow during crystallization. Polymorphs may also be obtained by heating or melting a compound of Formula I followed by gradual or fast cooling. The presence of polymorphs may be determined by solid NMR spectroscopy, IR spectroscopy, differential scanning calorimetry, powder x-ray diffraction or other techniques.

The present invention also includes all pharmaceutically acceptable isotopically-labelled compounds, which are identical to those described by Formula (I) but wherein one or more atoms are replaced by atoms having an atomic mass or mass number different from the atomic mass or mass number usually found in nature. Examples of isotopes that may be incorporated into compounds of the invention include isotopes of hydrogen, carbon, chlorine, fluorine, iodine, nitrogen, oxygen, sulfur, selenium and tellurium such as $^2H$, $^3H$, $^{11}C$, $^{13}C$, $^{14}C$, $^{36}Cl$, $^{18}F$, $^{123}I$, $^{13}N$, $^{15}N$, $^{17}O$, $^{18}O$, $^{35}S$, $^{79}Se$, and $^{128}Te$, respectively. It should be understood that compounds of the present invention, pro-drugs thereof, and pharmaceutical acceptable salts of the compounds or of the pro-drugs which contain the aforementioned isotopes and/or other isotopes of other atoms are within the scope of the invention. Certain isotopically labeled compounds of the present invention such as, for example, those incorporating a radioactive isotope such as $^3H$ and $^{14}C$, are useful in drug and/or substrate tissue distribution studies. Tritium, i.e. $^3H$, and carbon-14, i.e. $^{14}C$, are particularly preferred due their ease of preparation and detection. Further, substitution with heavier isotopes such as deuterium, i.e. $^2H$, can afford certain therapeutic advantages resulting from greater metabolic stability, for example, increased in vivo half-life or reduced dosage requirements, and hence may be preferred in some circumstances. Isotopically labeled compounds of Formula (I) of this invention and pro-drugs thereof can generally be prepared by carrying out the procedures disclosed in the Schemes and/or in the Examples by substituting a readily available isotopically labeled reagent for a non-isotopically labeled reagent.

The compounds of the invention may be isolated and used per se or in the form of their pharmaceutically acceptable salts or solvates. Pharmaceutically acceptable salts, as used herein in relation to the compounds of the present invention, include pharmacologically acceptable inorganic and organic salts of said compound. These salts can be prepared in-situ during the final isolation and/or purification of a compound (or pro-drug), or by separately reacting the compound (or pro-drug) with a suitable organic or inorganic acid and isolating the salt thus formed. A pharmaceutically acceptable salt of a compound of Formula (I) may be readily prepared by mixing together solutions of the compound of Formula (I) and the desired acid or base, as appropriate. The salt may precipitate from solution and be collected by filtration or may be recovered by evaporation of the solvent. The degree of ionization in the salt may vary from completely ionized to almost non-ionized.

Representative salts include, but are not limited to, acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate and the like. Other examples of representative salts include alkali or alkaline earth metal cations such as sodium, lithium, potassium, calcium, magnesium, and the like, as well as non-toxic ammonium, quaternary ammonium and amine cations including, but not limited to, ammonium, tetramethylammonium, tetraethylammonium, lysine, arginine, benzathine, choline, tromethamine, diolamine, glycine, meglumine, olamine and the like. The invention further includes mixtures of salt forms.

Compounds of the present invention may be administered as prodrugs. The term "prodrug" refers to a compound that is transformed in vivo to yield a compound of Formula I or a pharmaceutically acceptable salt or solvate of the compound. The transformation may occur by various mechanisms, such as via hydrolysis in blood.

A prodrug of a compound of Formula (I) may be formed in a conventional manner with one or more functional groups in the compound, such as an amino, hydroxyl or carboxyl group. For example, if a compound of the present invention contains a carboxylic acid functional group, a prodrug can comprise: (1) an ester formed by the replacement of a hydrogen of the acid group with a group such as $(C_1-C_6)$alkyl or $(C_6-C_{10})$aryl; (2) an activated ester formed by the replacement of the hydrogen of the acid group with groups such as —$(CR_2)COOR'$, where $CR_2$ is a spacer and R can be groups such as H or methyl and R' can be groups such as $(C_1-C_6)$alkyl or $(C_6-C_{10})$aryl; and/or (3) a carbonate formed by the replacement of the hydrogen of the acid with groups such as CHROCOOR' where R can be groups such as H or methyl and R' can be groups such as $(C_1-C_6)$alkyl or $(C_6-C_{10})$aryl.

Alternatively, certain compounds of Formula (I) may themselves act as prodrugs of other compounds of Formula I. Discussions regarding prodrugs and their use can be found in, for example, "Prodrugs as Novel Delivery Systems," T. Higuchi and W. Stella, Vol. 14 of the ACS Symposium Series, and Bioreversible Carriers in Drug Design, Pergamon Press, 1987 (ed. E B Roche, American Pharmaceutical Association). Further examples of replacement groups in accordance with the foregoing examples and examples of other prodrug types may be found in the aforementioned references.

FIGURES

FIG. 1 illustrates the cytotoxicity aptitude of rhenium complexes 9 and 10 against MCF-7 tumor cell line after 24 h incubation with the appropriate rhenium complex.

DETAILED DESCRIPTION

Figure 1:
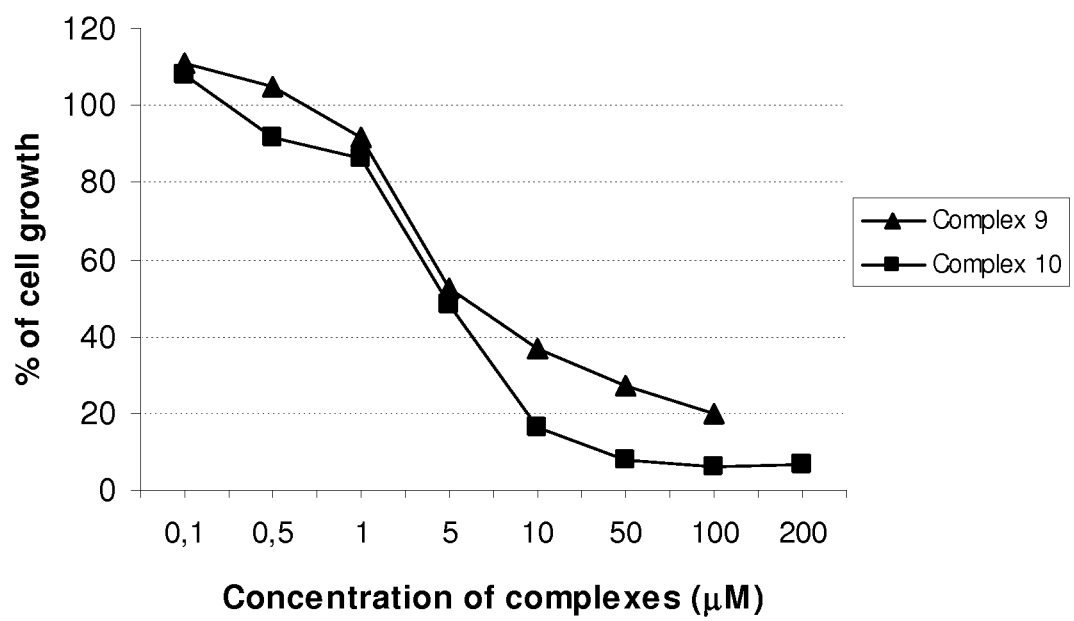

The following provides additional non-limiting details of compounds of Formula (I).

In general, the compounds of Formula (I) may be prepared by methods that include processes known in the chemical arts, particularly in light of the description contained herein in combination with the knowledge of the skilled person. Although other reagents, compounds or methods can be used in practice or testing, generalized methods for the preparation of the compounds of Formula (I) are illustrated by the following descriptions, Preparations, and reaction Schemes. Other processes for the preparation of compounds of Formula (I) are described in the experimental section.

The methods disclosed herein, including those outlined in the Schemes, Preparations, and Examples are for intended for illustrative purposes and are not to be construed in any manner as limitations thereon. Various changes and modifications will be obvious to those of skill in the art given the benefit of the present disclosure and are deemed to be within the spirit and scope of the present disclosure as further defined in the appended claims.

Unless otherwise indicated, the variables R, X, Y, Z, n, m, p and q that appear in the Preparations and Schemes are defined as above or as defined in the Claims.

Unless expressly defined otherwise, all technical and scientific terms used herein have the same meaning as commonly understood by one having ordinary skill in the art to which this disclosure belongs. Although specific embodiments of the present disclosure will be described with reference to the Schemes, Preparations and Examples, it should be understood that such embodiments are by way of example only and are merely illustrative of a small number of the many possible specific embodiments which can represent applications of the principles of the present disclosure.

Preparation of Bidentate Diseleno-Ethers Ligands:

The general method for the preparation of the bidentate diseleno-ethers ligands suitable to be used in combination with a rhenium metal to form a rhenium complex of Formula (I) was based on the reduction of the Se—Se or Se—CN bonds of the suitable starting material to form the nucleophilic RSe⁻ ions which can be reacted with various halogenoalkyls.

Ligands $PhSe(CH_2)_2SePh$ (1) and $PhSe(CH_2)_3SePh$ (2) have been prepared according to known methods available to the skilled artisan such as the one described in D. J. Gulliver et al., J. Chem. Soc. Perkin Trans. II (1984) 429-434 by reduction of $Ph_2Se_2$ with sodium hydroxymethanesulfonite in aqueous ethanol followed by reaction with 1,2-dibromoethane or 1,3-dibromopropane, respectively.

In Scheme 1 other bidentate diseleno-ethers ligands suitable to be used in combination with a rhenium metal to form a rhenium complex of Formula (I) may also be prepared by reduction of the Se—Se or Se—CN bonds of the suitable starting material to form the nucleophilic RSe⁻ ions which can further react with the appropriate halogenoalkyl.

Ligand $HOOC—CH_2Se(CH_2)_2SeCH_2—COOH$ (3) was prepared according to the method described in L. R. M. Pitombo et al., Rev. Latinoam. Quim. 13 (1982) 108-109, and the same method was employed to prepare ligand $HOOC—CH_2Se(CH_2)_3SeCH_2—COOH$ (4) by treatment of propylene diselenocyanate $(NCSe(CH_2)_3SeCN)$ with sodium hydroxide (NaOH) and sodium borohydride $(NaBH_4)$, followed by reaction with sodium bromoacetate, according to Scheme 1.

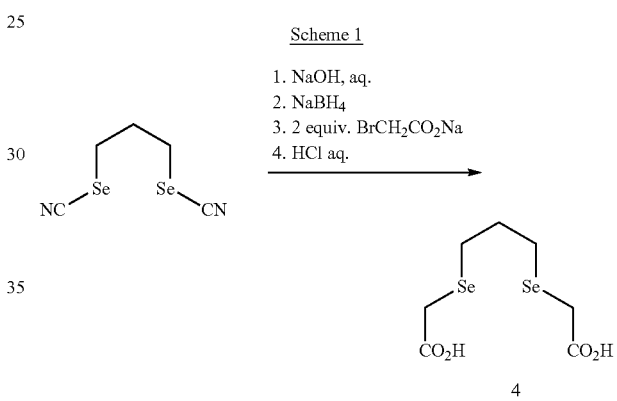

Preparation of Rhenium Complexes According to the Present Invention:

Re(I) complexes were synthesized by reaction of commercially available $Re(CO)_5Cl$ with the corresponding ligands at reflux in THF according to methods described in N. A. Illán-Cabeza et al., J. Inorg. Biochem. 99 (2005) 1637-1645, D.-L. Ma et al., Inorg. Chem. 46 (2007) 740-749, K. E. Elwell et al, Bioorg. Med. Chem. 14 (2006) 8692-8700 and E. W. Abel et al., J. Chem. Soc. Dalton Trans. (1982) 2065-2072.

The reaction of $Re(CO)_5Cl$ with ligands 1, 2, 3 and 4 led to the formation of complexes 5, 6, 7 and 8, respectively.

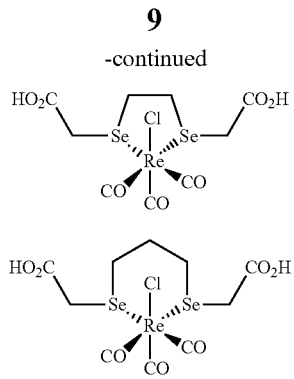

Figure 2:
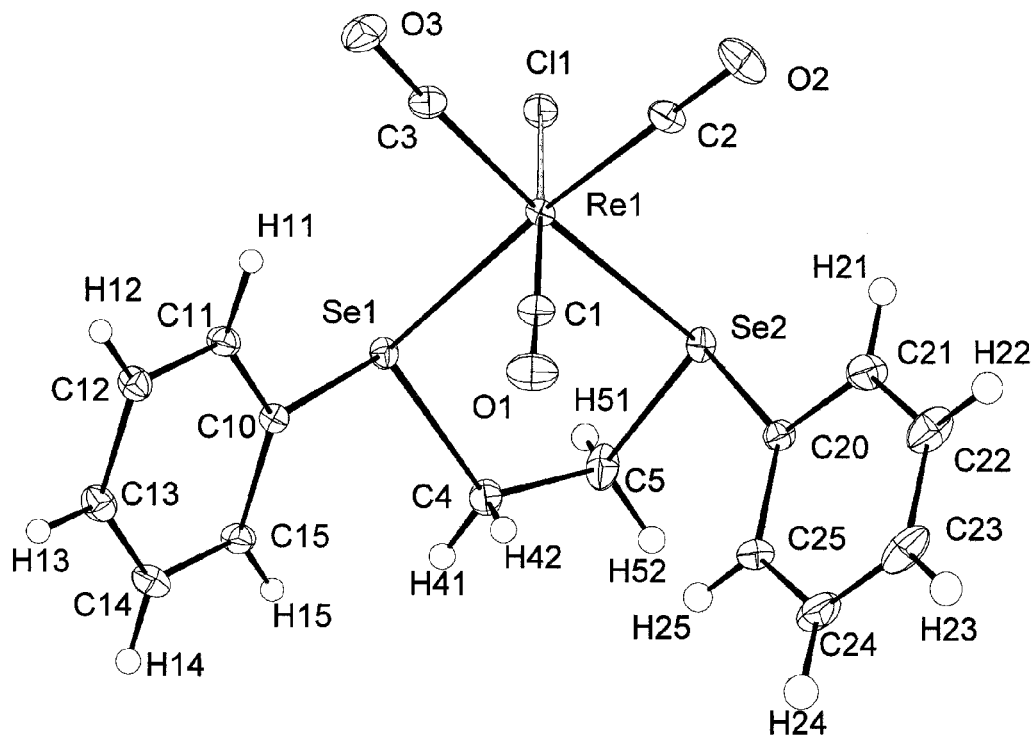
FIG. 2a shows the labeled CAMERON diagrams of $C_{17}H_{14}O_3ClSe_2Re$ (complex 5). Ellipsoids are drawn at a 50% probability level.
FIG. 2b shows the labeled CAMERON diagrams of $C_{18}H_{16}O_3ClSe_2Re$ (complex 6). Ellipsoids are drawn at a 50% probability level.
Figure 2:
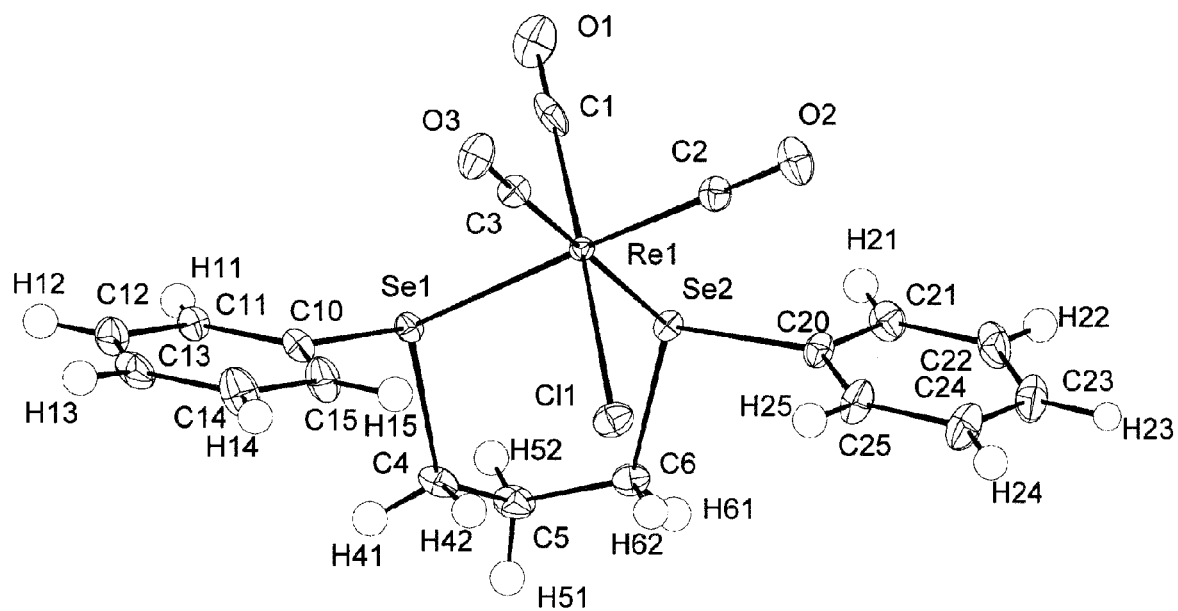

Chemical structures of complexes 5 and 6 were established through single-crystal X-ray diffraction analysis (selected bond parameters are provided in Tables 4 and 5 in the experimental section hereinbelow and labeled CAMERON diagrams are shown in FIG. 2) whereas structures of complexes 7 and 8 were determined through elemental analysis, infrared spectroscopy (IR), $^1$H-NMR and mass spectroscopy (MS). In this respect, the facial arrangement of the carbonyl groups in all complexes is evidenced from the CO-stretching absorptions in the IR spectra. The three strong v(CO) stretching bands appear in the region of 2030-1860 cm$^{-1}$, indicating the presence of the fac-[Re(CO)$_3$]$^+$ core.

Biological Activity Against Several Human Tumor Cell Lines of Complexes 9 and 10 (the Disodium Salts of Complexes 7 and 8, Respectively)

The antiproliferative activity of representative rhenium complexes of the invention on four human solid tumor cells: HT 29 (colorectal cancer cells), MCF-7 (hormone-dependent breast cancer cells), A 549S (lung adenocarcinoma cells) and HeLa (solid uterine carcinoma cells) was studied following a procedure depicted in the present Experimental section below.

As illustrated by FIG. 1, the pattern of cytotoxic activity of these two complexes shows high activities against MCF-7 breast cancer cells, complex 10 being the most effective with an IC$_{50}$ of 4.75 μM. As shown in Table 3 below, complex 10 was most effective on MCF-7 breast cancer cells.

TABLE 3

| Cell lines | IC$_{50}$ (μM) |
|---|---|
| HeLa | 75.12 |
| A 549S | 131.5 |
| HT 29 | >500 |
| MCF-7 | 4.75 |

One of ordinary skill in the art will appreciate that in some cases protecting groups may be required during synthesis. After a particular target molecule or intermediate is made or at some specific step later in a synthetic route, the protecting group can be removed by methods well known to those of ordinary skill in the art, such as described in Greene and Wuts, Protective Groups in Organic Synthesis, (3rd Ed, John Wiley & Sons, 1999).

The compounds of the present disclosure intended for pharmaceutical use may be administered alone or in combination with one or more other compounds of the invention or in combination with one or more other drugs (or as any combination thereof), in particular with one or more other anti-cancer agents. Generally, the compound(s) will be administered as a formulation in association with one or more pharmaceutically acceptable excipients.

Preferably, the anti-cancer agent is a chemical or biological substance which is clinically shown to treat cancer. More preferably, the anti-cancer agent is selected from the group consisting of actinomycin D, adriamycin, amsacrine, ara-C, 9-(3-D-arabinosyl-2-fluoroadenine, BCNU, bleomycin, camptothecin, carboplatin, 2-chloro-2-deoxyadenosine, CPT-11, cyclophosphamide, docetaxel, doxorubicin, edotecarin, etoposide, fludarabine, 5-fluorouracil (5-FU), gemcitabine, HU-Gemzar, Irinotecan, methotrexate, 6-Mpurine, mytomicin-C, paclitaxel, cis-platin, SN-38, taxol, thiotepa, 6-thioguanine, trimetrexate vinblastine, vincristine, and VP-16.

In a particular embodiment, the anti-cancer agent is a DNA damaging agent. Preferably, the "DNA damaging agent" is a chemical or biological substance that is clinically shown to treat cancer. More preferably, the DNA damaging agent is selected from the group consisting of alkylating agents, antimetabolites, antitumor antibiotics, platinum analogs and other metal analogs such as gallium, gold, ruthenium, arsenic, palladium, cobalt, copper and lanthanum analogs, topoisomerase I inhibitors and topoisomerase II inhibitors.

Preferably, the alkylating agent is selected from the group consisting of apaziquone, altretamine, brostallicin, bendamustine, busulfan, carboquone, carmustine, chlorambucil, chlormethine, cyclophosphamide, estramustine, fotemustine, glufosfamide, ifosfamide, lomustine, mafosfamide, mechlorethamine oxide, mecillinam, melphalan, mitobronitol, mitolactol, nimustine, nitrogen mustard N-oxide, pipobroman, ranimustine, temozolomide, thiotepa, treosulfan, and trofosframide.

Preferably, the antimetabolite is selected from the group consisting of Alimta, Ara-C, 5-azacitidine, capecitabine, carmofur, cladribine, clofarabine, cytarabine, cytosine arabinoside, decitabine, disodium premetrexed, doxifluridine, eflornithine, enocitabine, ethynylcytidine, floxuridine, fludarabine, 5-fluorouracil (5-FU), gemcitabine, hydroxyurea, leucovorin, melphalan, 6-mercaptopurine, methotrexate, mitoxantrone, 6-Mpurine, pentostatin, pelitrexol, raltitrexed, riboside, methotrexate, mercaptopurine, nelarabine, nolatrexed, ocfosfate, tegafur, 6-thioguanine (6-TG), tioguanine, triapine, trimetrexate, vidarabine, vincristine, vinorelbine and UFT.

Preferably, the antitumor antibiotic is selected from the group consisting of aclarubicin, actinomycin D, amrubicin, annamycin, adriamycin, bleomycin, dactinomycin, daunorubicin, doxorubicin, elsamitrucin, epirubicin, galarubicin, idarubicin, mitomycin C, mycophenolic acid, nemorubicin, neocarzinostatin, pentostatin, peplomycin, pirarubicin, rebeccamycin, stimalamer, streptozocin, valrubicin and zinostatin.

Preferably, the platinum analogue is selected from the group consisting of carboplatin (Paraplatin), cisplatin, Eloxatin (oxaliplatin, Sanofi), eptaplatin, lobaplatin, nedaplatin, satraplatin and picoplatin, but other platinum compounds may be potentiated by the rhenium complexes of the invention.

Preferably, the topoisomerase I inhibitor is selected from the group consisting of BN-80915 (Roche), camptothecin, CPT-11, edotecarin, exatecan, irinotecan, orathecin (Supergen), SN-38, and topotecan.

Preferably, the toposimerase II inhibitor is selected from amsacrine, etoposide, etoposide phosphate and epirubicin (Ellence).

In another embodiment, the anti-cancer agent is a mitotic inhibitor. Preferably, the mitotic inhibitor is selected from the group consisting of docetaxel (Taxotere), estramustine, paclitaxel, razoxane, taxol, teniposide, vinblastine, vincristine, vindesine, vinorelbine and vinflunine.

In another embodiment, the anti-cancer agent is an anti-angiogenesis agent. Preferably, the anti-angiogenesis agent is selected from EGF inhibitors, EGFR inhibitors, VEGF inhibitors, VEGFR inhibitors, TIE2 inhibitors, IGF1R inhibitors, COX-II (cyclooxygenase II) inhibitors, MMP-2 (matrix-metalloprotienase 2) inhibitors, and MMP-9 (matrix-metalloprotienase 9) inhibitors.

Preferred VEGF inhibitors, include for example, Avastin (bevacizumab), an anti-VEGF monoclonal antibody of Genentech, Inc. of South San Francisco, Calif. Additional VEGF inhibitors include CP-547,632 (Pfizer Inc., NY, USA), axitinib (Pfizer Inc.), ZD-6474 (AstraZeneca), AEE788 (Novartis), AZD-2171, VEGF Trap (Regeneron/Aventis), Vatalanib (also known as PTK-787, ZK-222584: Novartis & Schering AG), Macugen (pegaptanib octasodium, NX-1838, EYE-001, Pfizer Inc./Gilead/Eyetech), IM862 (Cytran Inc. of Kirkland, Wash., USA); and angiozyme, a synthetic ribozyme from Ribozyme (Boulder, Colo.) and Chiron (Emeryville, Calif.) and combinations thereof.

Preferred EGRF inhibitors include, but are not limited to Iressa (gefitinib, AstraZeneca), Tarceva (erlotinib or OSI-774, OSI Pharmaceuticals Inc.), Erbitux (cetuximab, Imclone Pharmaceuticals, Inc.), EMD-7200 (Merck AG), ABX-EGF (Amgen Inc. and Abgenix Inc.), HR3 (Cuban Government), IgA antibodies (University of Erlangen-Nuremberg), TP-38 (IVAX), EGFR fusion protein, EGF-vaccine, anti-EGFr immunoliposomes (Hermes Biosciences Inc.) and combinations thereof.

Other anti-angiogenic agent include acitretin, fenretinide, thalidomide, zoledronic acid, angiostatin, aplidine, cilengtide, combretastatin A-4, endostatin, halofuginone, rebimastat, removab, Revlimid, squalamine, ukrain, Vitaxin and combinations thereof.

In another embodiment, the anti-cancer agent is a pan kinase inhibitor. Preferred pan kinase inhibitors include Sutent™ (sunitinib), described in U.S. Pat. No. 6,573,293.

In another embodiment, the anti-cancer agent is selected from pan Erb receptor inhibitors or ErbB2 receptor inhibitors, such as CP-724,714 (Pfizer, Inc.), CI-1033 (canertinib, Pfizer, Inc.), Herceptin (trastuzumab, Genentech Inc.), Omitarg (2C4, pertuzumab, Genentech Inc.), TAK-165 (Takeda), GW-572016 (Ionafarnib, GlaxoSmithKline), GW-282974 (GlaxoSmithKline), EKB-569 (Wyeth), PKI-166 (Novartis), dHER2 (HER2 Vaccine, Corixa and GlaxoSmithKline), APC8024 (HER2 Vaccine, Dendreon), anti-HER2/neu bispecific antibody (Decof Cancer Center), B7.her2.IgG3 (Agensys), AS HER2 (Research Institute for Rad Biology & Medicine), trifunctional bispecific antibodies (University of Munich) and mAB AR-209 (Aronex Pharmaceuticals Inc) and mAB 2B-1 (Chiron) and combinations thereof.

In another embodiment, the anti-cancer agent is selected from Genasense (augmerosen, Genta), Panitumumab (Vectibix/Amgen), Zevalin (Schering), Bexxar (Corixa/GlaxoSmithKline), Abarelix, Alimta, EPO 906 (Novartis), discodermolide (XAA-296), ABT-510 (Abbott), Neovastat (Aeterna), enzastaurin (Eli Lilly), Combrestatin A4P (Oxigene), ZD-6126 (AstraZeneca), flavopiridol (Aventis), CYC-202 (Cyclacel), AVE-8062 (Aventis), DMXAA (Roche/Antisoma), Thymitaq (Eximias), Temodar (temozolomide, Schering Plough) and Revilimd (Celegene) and combinations thereof.

In another embodiment, the anti-cancer agent is selected from CyPat (cyproterone acetate), Histerelin (histrelin acetate), Plenaixis (abarelix depot), Atrasentan (ABT-627), Satraplatin (JM-216), thalomid (Thalidomide), Theratope, Temilifene (DPPE), ABI-007 (paclitaxel), Evista (raloxifene), Atamestane (Biomed-777), Xyotax (polyglutamate paclitaxel), Targetin (bexarotine) and combinations thereof.

In another embodiment, the anti-cancer agent is selected from Trizaone (tirapazamine), Aposyn (exisulind), Nevastat (AE-941), Ceplene (histamine dihydrochloride), Orathecin (rubitecan), Virulizin, Gastrimmune (G17DT), DX-8951f (exatecan mesylate), Onconase (ranpirnase), BEC2 (mitumoab), Xcytrin (motexafin gadolinium) and combinations thereof.

In another embodiment, the anti-cancer agent is selected from CeaVac (CEA), NeuTrexin (trimetresate glucuronate) and combinations thereof. Additional anti-tumor agents may be selected from the following agents, OvaRex (oregovomab), Osidem (IDM-1), and combinations thereof. Additional anti-tumor agents may be selected from the following agents, Advexin (ING 201), Tirazone (tirapazamine), and combinations thereof. Additional anti-tumor agents may be selected from the following agents, RSR13 (efaproxiral), Cotara (131I chTNT 1/b), NBI-3001 (IL-4) and combinations thereof. Additional anti-tumor agents may be selected from the following agents, Canvaxin, GMK vaccine, PEG Interon A, Taxoprexin (DHA/paclitaxel), and combinations thereof.

The term "excipient" is used herein to describe any ingredient other than the compound(s) of the invention and includes ingredients such as vehicles, carriers, diluents, preservatives and the like. The choice of excipient(s) will largely depend on factors such as the particular mode of administration, the effect of the excipient(s) on solubility and stability, and the nature of the dosage form.

A pharmaceutical composition of the invention, for example, includes forms suitable for oral administration as a tablet, capsule, pill, powder, sustained release formulations, solution, suspension, or for parenteral injection as a sterile solution, suspension or emulsion. Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

In one preferred embodiment, the compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations, such as tablets, capsules containing particulates, liquids, or powders; lozenges (including liquid-filled), chews; multi- and nano-particulates; gels, solid solution, liposome, films (including muco-adhesive), ovules, sprays and liquid formulations. Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet. The compounds of the invention may also be used in fast-dissolving, fast-disintegrating dosage forms such as those described in Expert Opinion in Therapeutic Patents, 11 (6), 981-986 by Liang and Chen (2001).

In another preferred embodiment, the compounds of the invention may be administered by parenteral injection. Exemplary parenteral administration forms include sterile solutions, suspensions or emulsions of the compounds of the invention in sterile aqueous media, for example, aqueous propylene glycol or dextrose. In another embodiment, the parenteral administration form is a solution. Such parenteral dosage forms can be suitably buffered, if desired.

Dosage regimens of the compounds and/or pharmaceutical composition of the invention may be adjusted to provide the optimum desired response. For example, a single bolus may be administered, several divided doses may be administered over time or the dose may be proportionally reduced or increased as indicated by the exigencies of the therapeutic situation. The appropriate dosing regimen, the amount of each dose administered and/or the intervals between doses will depend upon the compound of the invention being used, the type of pharmaceutical composition, the characteristics of the subject in need of treatment and the severity of the condition being treated.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It should be noted that variation in the dosage will depend on the compound employed, the mode of administration, the treatment desired and the disorder (severity and type) to be treated or alleviated. The present invention also encompasses sustained release compositions and 'flash' formulations, i.e. providing a medication to dissolve in the mouth.

It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regiments for administration of the chemotherapeutic agent are well-known in the relevant art and would be understood to be encompassed by the skilled artisan once provided the teachings disclosed herein.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, a pharmaceutical composition of the invention may comprise between 0.1% and 100% (w/w) active ingredient. In addition to the active ingredient, a pharmaceutical composition of the invention may further comprise one or more additional pharmaceutically active agents.

PREPARATIVE EXAMPLES

The compounds described below are non-limiting Examples of compounds encompassed by Formula I that were prepared and characterized according to one or more of the procedures outlined below. The preparation of various intermediates is also described.

In the discussions below, the following abbreviations are used:

The $^1$H NMR and $^{13}$C NMR spectra were recorded at 300 and 75.5 MHz, respectively, on a Bruker Advance spectrometer and were in all cases consistent with the proposed structures. Characteristic chemical shifts ([delta]) are given in parts-per-million using conventional abbreviations for the designation of major peaks: e.g., s, singlet; d, doublet; t, triplet; q, quartet; m, multiplet; br, broad.

Mass spectra were recorded with a Bruker Daltonics micro TOF (ESI; positive or negative modes; capillary voltage: 4.8 kV; nebulizer pressure: 0.2 bar; desolvation temperature: 180° C.; desolvation gas flow rate: 4.5 l.min$^{-1}$).

The IR spectra in the range of 3500-600 cm$^{-1}$ were obtained on a Bruker IFS28FT as neat films.

A Perkin-Elmer 2400 II elemental analyzer was used to perform the microanalyses.

Room or ambient temperature refers to 20-25° C.

Unless stated otherwise, all non-aqueous reactions were run under a nitrogen atmosphere and commercial reagents were utilized without further purification.

The terms 'concentration' or 'concentration at reduced pressure' or 'in vacuo' mean that a rotary evaporator and/or vacuum pump were used.

Preparation of ligand 3,7-diselenanonanedioic acid (4)

A mixture of powdered Selenium (Se) (2.0 g, 25.31 mmol) and potassium cyanide (KCN) (1.5 g, 23.04 mmol) in 60 ml of acetone was stirred at reflux for 2 days. After removal of the unreacted Se by filtration, 1,3-dibromopropane (0.5 g, 9.91 mmol) was added and the solution stirred at reflux for 4 h. Acetone was then removed under reduced pressure, the residual oil was dissolved in $CH_2Cl_2$ and the resulting solution was filtered. After removal of $CH_2Cl_2$ under reduced pressure, pale yellow crystals were obtained, which were washed with diethyl ether and dried under vacuum to give colorless crystals of the desired compound propylene diselenocyanate. Yield: 1.220 g (50%); m.p. 49° C.; NMR ($CDCl_3$): δ 2.59 (q, $^3J_{HH}$=6.8 Hz, 2H, $CH_2CH_2CH_2$), 3.26 (t, $^3J_{HH}$=6.8 Hz, 4H, $SeCH_2$); $^{13}$C NMR ($CDCl_3$): δ 27.5 [s (93%) and d (7%), $J_{77_{Se}C}$=53.8 Hz, $SeCH_2$], 31.3 (s, $CH_2CH_2CH_2$), 100.6 (s, SeCN).

To a solution of NaOH (0.500 g, 12.50 mmol) in 15 ml of a mixture ethanol/water (2/1) was added the above prepared propylene diselenocyanate (0.466 g, 1.85 mmol) and the mixture was stirred for 2 h at room temperature to give an orange solution. $NaBH_4$ (0.500 g, 13.22 mmol) was added and the mixture was stirred for 1 h at room temperature and a further 1 h at 50° C. to give an orange solution and a yellow precipitate. Sodium 2-bromoacetate (0.596 g, 3.71 mmol) was added and the mixture was stirred overnight at room temperature. The white precipitate was removed by filtration and the colorless solution was concentrated under reduced pressure to 5 ml. The pH was adjusted to pH 1 by addition of a 6 M HCl solution. The resulting white precipitate and the remaining aqueous solution were extracted with $CH_2Cl_2$ and the combined organic layers were washed with water and dried over $MgSO_4$. After removal of the solvents under reduced pressure, the residual white solid was washed with cyclohexane and dried under vacuum to give the desired product 4. Yield: 0.380 g (65%); m.p. 75° C.; IR 2860 (m), 2640 (m), 2510 (m), 1678 (s), 1425 (m), 1389 (m), 1271 (s), 1227 (m), 1178 (m), 1159 (m), 1116 (m), 935 (s), 765 (m), 747 (m), 648 (s) $cm^{-1}$; $^1H$ NMR (DMSO-$d_6$): δ 2.00 (quint., 2H, $CH_2CH_2CH_2$), 2.80 (t, $^3J_{HH}$=6.8 Hz, 4H, $CH_2CH_2CH_2$), 3.20 [s (93%) and d (7%), $^2J_{77_{SeH}}$=15.1 Hz, 4H, $SeCH_2CO_2H$], 12.50 (br s, 2H, $CO_2H$); $^{13}C$ NMR (DMSO-$d_6$): δ 22.5 [s (93%) and d (7%), $J_{77_{Se}C}$=67.0 Hz, $SeCH_2$], 24.3 [s (93%) and d (7%), $J_{77_{Se}C}$=61.8 Hz, $SeCH_2$], 29.6 (s, $CH_2CH_2CH_2$), 172.7 (s, $CO_2H$).

Alternatively, compound (4) was prepared through alkylation of the disodium salt of propane-1,3-diselenol with bromoacetic acid methyl ester followed by aqueous lithium hydroxide hydrolysis according to the following procedure.

Alternative preparation of ligand 3,7-diselenanonanedioic acid (4)

Preparation of (3-Carboxymethylselanyl-propylselanyl)-acetic acid dimethyl ester (a.k.a. dimethyl 3,7-diselenanonanedioate): To a solution of 1,3-bis-selenocyanato-propane (1.0 g, 3.96 mmol) in absolute ethanol (20 mL) was added bromoacetic acid methyl ester (1.23 g, 8.0 mmol). The mixture was stirred under nitrogen until complete dissolution. Sodium borohydride (303 mg, 8.0 mmol) was then added in one portion. The reaction mixture was stirred at room temperature for 16 h. The white precipitate was filtered off on a sintered glass funnel and the yellowish filtrate was concentrated under reduced pressure to yield a pale yellow oil. This was used in the next step without further purification. Yield: 1.12 g (82%); $^1H$ NMR (CDCl$_3$): δ 3.72 (s, 6H, $OCH_3$), 3.17 (s, 4H, $CH_2CO_2Me$), 2.82 (t, J=7.2 Hz, 4H, $SeCH_2CH_2CH_2Se$), 2.0 (quint, J=7.2 Hz, 2H, $SeCH_2CH_2CH_2Se$).

Preparation of (3-Carboxymethylselanyl-propylselanyl)-acetic acid (a.k.a. 3,7-diselenanonanedioic acid): To a solution of crude (3-carboxymethylselanyl-propylselanyl)-acetic acid dimethyl ester (692 mg, 2.0 mmol) in THF (3 mL) was added LiOH.H$_2$O (336 mg, 8.0 mmol) in 2 mL of water. Methanol was then added until a homogeneous solution was obtained. The reaction mixture was stirred at room temperature for 16 h and the solvents were removed under reduced pressure. The pH of the reaction mixture was adjusted to pH=1-2 using a 3N HCl aqueous solution and the mixture was extracted with ethyl acetate. The combined organic layers were dried over $MgSO_4$ and concentrated under reduced pressure. The oily residue was taken into a small amount of $CH_2Cl_2$ and precipitated with petroleum ether. The resulting solid was filtered, washed with diethyl ether and dried under vacuum to give 540 mg (85% yield) of the desired product (4) whose spectroscopic data were in full agreement with the data reported above.

As stated above, ligands 1, 2 and 3 were prepared according to a known method described in D. J. Gulliver et al., J. Chem. Soc. Perkin Trans. II (1984) 429-434 and L. R. M. Pitombo et al., Rev. Latinoam. Quim. 13 (1982) 108-109.

Preparation of Rhenium Complexes 5 to 10

Preparation of Complex 5

To a solution of ligand 1 [$PhSe(CH_2)_2SePh$] (103 mg, 0.303 mmol) in 15 ml of THF was added $Re(CO)_5Cl$ (110 mg, 0.304 mmol) and the mixture was stirred at reflux overnight. THF was removed under reduced pressure and the residual white powder was washed with cyclohexane and diethyl ether and dried under vacuum to afford the desired complex 5. Yield: 114 mg (58%); Anal. Calc. for: $C_{17}H_{14}O_3ClSe_2Re$: C, 31.61; H, 2.18. Found: C, 31.26; H, 2.19; MS (positive mode): 669 ($[M+Na]^+$), 611 ($[M-Cl]^+$), 583 ($[M-Cl-CO]^+$), 555 ($[M-Cl-2CO]^+$); IR: 2020 (s), 1923 (s), 1898 (s), 1575 (m), 1478 (m), 1436 (m), 1412 (m), 1099 (m), 1071 (m), 1021 (m), 837 (m), 745 (s), 688 (s), 667 (m), 631 (m), 616 (m) $cm^{-1}$; NMR (CDCl$_3$): δ 3.20 (m, 2H), 3.65 (m, 2H), 7.35-7.65 (m, 10H). Colorless crystals suitable for X-ray analysis were obtained from methylene chloride.

Preparation of Complex 6

To a solution of ligand 2 [$PhSe(CH_2)_3SePh$] (91.3 mg, 0.258 mmol) in 15 ml of THF was added $Re(CO)_5Cl$ (85 mg, 0.235 mmol) and the mixture was stirred at reflux overnight. THF was removed under reduced pressure the residual white powder was washed with cyclohexane and diethyl ether and dried under vacuum to afford the desired complex 6. Yield: 138 mg (89%); Anal. Calc. for: $C_{18}H_{16}O_3ClSe_2Re$: C, 32.76; H, 2.44. Found: C, 32.62; H, 2.45; MS (positive mode): 625 ($[M-Cl]^+$, see FIG. 7); IR: 2026 (s), 1929 (s), 1906 (s), 1578 (m), 1478 (m), 1439 (m), 1219 (m), 1070 (m), 1022 (m), 999 (m), 805 (m), 737 (s), 690 (s), 669 (m), 639 (m) $cm^{-1}$; $^1H$ NMR (CDCl$_3$): δ 1.8-4.6 (seven methylenes resonances, 6H, see FIG. 8), 7.2-8.0 (m, 10H). Colorless crystals suitable for X-ray analysis were obtained from methylene chloride.

Preparation of Complex 7

To a solution of ligand 3 (3,6-diselenaoctanedioic acid, 0.105 g, 0.35 mmol) in 15 ml of THF was added $Re(CO)_5Cl$ (0.125 g, 0.35 mmol) and the mixture was stirred at reflux overnight. THF was removed under reduced pressure, the residual white powder was washed with cyclohexane and diethyl ether and dried under vacuum to afford the desired complex 7. Yield: 0.151 g (72%); Anal. Calc. for $C_9H_{10}O_7ClSe_2Re$: C, 17.73; H, 1.65. Found: C, 17.74; H, 1.69; MS (positive mode): 575 ($[M-Cl]^+$); IR: 3170-2360 (m), 2032 (s), 1943 (m), 1914 (s), 1692 (s), 1416 (m), 1366 (m), 1309 (s), 1284 (m), 1208 (m), 1172 (m), 1140 (m), 1094 (m), 892 (m), 853 (m), 798 (s), 706 (m), 660 (m), 631 (m) $cm^{-1}$; $^1H$ NMR (DMSO-$d_6$): δ 3.05 (s, 2H), 3.25 (s, 2H), 3.35 (br s, 4H).

Preparation of Complex 8

To a solution of ligand 4 (3,7-diselenanonanedioic acid, 0.135 g, 0.43 mmol) in 15 ml of THF was added $Re(CO)_5Cl$ (0.154 g, 0.43 mmol) and the mixture was stirred at reflux overnight. THF was removed under reduced pressure and the residual white powder was washed with cyclohexane and dried under vacuum to afford the desired complex 8. Yield: 0.240 g (90%); Anal. Calc. for $C_{10}H_{12}O_7ClSe_2Re$: C, 19.25; H, 1.94. Found: C, 19.46; H, 1.97; MS (positive mode): 589 ($[M-Cl]^+$); IR: 3330-2340 (m), 2029 (s), 1935 (s), 1895 (s), 1731 (s), 1699 (s), 1415 (m), 1351 (m), 1282 (m), 1249 (m), 1206 (s), 1186 (m), 1092 (m), 834 (m), 785 (m), 752 (m), 670 (m), 637 (m), 624 (s), 605 (m) $cm^{-1}$; $^1H$ NMR (CD$_3$OD): δ 2.6-3.9 (m, 10H).

Preparation of Complex 9 (Disodium Salt of Complex 7)

To a solution of complex 7 (0.330 g, 0.545 mmol) in 20 ml of ethanol was added $Na_2CO_3$ (0.100 g, 1.20 mmol) and the mixture was stirred overnight at room temperature. The excess of $Na_2CO_3$ was removed by filtration and ethanol was evaporated under reduced pressure. The residual white powder was washed with diethyl ether and dried under vacuum to afford the desired product. Yield: 0.320 g (90%); Anal. Calc. for $C_9H_8O_7ClNa_2Se_2Re$, 0.25 $C_2H_5OH$: 17.16; H, 1.44. Found: C, 17.25; H, 1.99; MS (negative mode): 573 ([M−2Na−Cl]⁻, see Scheme 2); IR: 2031 (s), 1909 (s), 1893 (s), 1595 (s), 1374 (s), 1345 (s), 1190 (m), 1134 (m), 1089 (m), 1041), 926 (m), 870 (m), 791 (m), 625 (m), 606 (m) cm⁻¹.

Preparation of Complex 10 (Disodium Salt of Complex 8)

To a solution of complex 8 (0.343 g, 0.55 mmol) in 20 ml of ethanol was added $Na_2CO_3$ (0.122 g, 1.15 mmol) and the mixture was stirred overnight at room temperature. The excess of $Na_2CO_3$ was removed by filtration and ethanol was evaporated under reduced pressure. The residual white powder was washed with diethyl ether and dried under vacuum to afford the desired product. Yield: 0.330 g (90%); Anal. Calc. for $C_{10}H_{10}O_7ClNa_2Se_2Re$, 0.25 $C_2H_5OH$: C, 18.57; H, 1.71. Found: C, 18.95; H, 2.18; MS (negative mode): 587 ([M−2Na−Cl]⁺, see Scheme 2); IR: 2016 (s), 1909 (s), 1862 (s), 1572 (s), 1418 (m), 1374 (s), 1344 (s), 1232 (m), 1192 (m), 1092 (m), 933 (m), 874 (m), 828 (m), 731 (m), 683 (m) cm⁻¹.

Biological Assays

The MTT/IC50 was used to determine the chemosensitivity of the four human cancer cell lines (cytotoxicity was estimated in terms of cellular growth inhibition and IC50 represents the concentration (μM) required to reduce the viable cell population by half). The method is based on the ability of living cells to reduce MIT tetrazolium salt [3-(4,5-dimethylthiazole-2-yl)-2,5-diphenyltetrazolium bromide] into MIT formazan [1-(4,5-dimethylthiazol-2-yl)-3,5-diphenylformazan] by the mitochondrial enzyme succinate dehydrogenase of the active living cells. Samples of the studied complexes were dissolved in either $H_2O$ or in a mixture DMSO/$H_2O$ 10/90 according to their respective solubility at the appropriate concentration and were added to the appropriate tumour cells culture. After 24 hours incubation, the culture medium was carefully aspirated, and MIT (Sigma-Aldrich) (0.5 mg/ml) in solution into RPMI medium without Phenol Red was added to each well. After 4 hrs incubation at 37° C., the medium was removed and the formazan crystals formed by living cells were dissolved in 0.1 ml of DMSO. The absorbance was measured in each well at 570 nm with a SpectraMax 250 microplate reader (Molecular Devices, USA). The 50% inhibitory concentration (IC50) was defined as the concentration that caused a 50% of treated cell death compared to control cells.

X-Ray Diffraction Measurements

Diffraction data were collected with a Bruker-SMART three-axis diffractometer equipped with a SMART 1000 CCD area detector using graphite monochromated Mo Kα X-radiation (wavelength λ=0.71073 Å) at 100 K. Data collection and processing were performed using Bruker SMART programs and empirical absorption correction was applied using SADABS computer program as described in ASTRO (5.00), SAINT (5.007) and SADABS (5.007), Data Collection and Processing Software for the SMART System (5.054), Siemens (BRUKER-AXS) Analytical X-ray Instruments Inc., Madison, Wis., 1998. The structure was solved by direct methods using SIR97 as described in A. Altomare et al., J. Appl. Crystallogr. 32 (1999) 115-119, and refined by full-matrix least-squares based on F using CRYSTALS software according to D. J. Watkin et al., Chemical Crystallography Laboratory, University of Oxford, UK, 2001. The molecule was drawn using the CAMERON program as described in D. J. Watkin et al., Chemical Crystallography Laboratory, University of Oxford, UK, 1996. All non-hydrogen atoms were anisotropically refined. Hydrogen atoms were located in difference Fourier maps. H atoms were refined isotropically with $U_{iso}$=1.20 $U_{eq}$ where $U_{eq}$ is the equivalent isotropic atomic displacement parameter of the attached atom. Crystal parameters, data collection and the refinement details of compounds 5 and 6 are reported in Tables 4 and 5 below.

Compound 5: a monoclinic unit cell: a=15.1525(10), b=7.6292(10), c=16.8518(10) Å, α=90°, β=112.850(10)°, γ90°, V=1494.4(3) Å³, Z=4 and d(calc)=2388 cm⁻³. For all 8093 unique reflections the final anisotropic full-matrix least squares refinement on F for 218 variables converged at R[F] =0.0200 and wR [F]=0.0217 with a goodness of fit of 1.0771.

Compound 6: an orthorhombic unit cell: a=14.522(1), b=13.105(1), c=20.470(1) Å, a=β=γ=90°, V=3895.4(4) Å³, Z=8 and d(calc)=2.25 g·cm⁻³. For all 5931 unique reflections the final anisotropic full-matrix least squares refinement on F for 226 variables converged at R [F]=0.022612 and wR [F]=0.0232609 with a goodness of fit of 1.0815.

TABLE 4

Selected bond distances (Å) and bond angles (°) for $C_{17}H_{14}O_3Cl Se_2Re$ (5)

| Bond lengths | | Bond angles | | Bond angles | |
|---|---|---|---|---|---|
| Re(1)—Se(1) | 2.6050(4) | Se(1)—Re(1)—Se(2) | 85.11(2) | C(2)—Re(1)—Cl(1) | 95.98(7) |
| Re(1)—Se(2) | 2.5939(3) | Se(1)—Re(1)—C(1) | 90.42(6) | C(3)—Re(1)—Cl(1) | 94.22(7) |
| Re(1)—C(1) | 1.899(2) | Se(2)—Re(1)—C(1) | 94.58(7) | Re(1)—Se(1)—C(4) | 99.21(7) |
| Re(1)—C(2) | 1.922(2) | Se(1)—Re(1)—C(2) | 174.93(7) | Re(1)—Se(1)—C(10) | 109.97(6) |
| Re(1)—C(3) | 1.921(2) | Se(2)—Re(1)—C(2) | 89.83(7) | C(4)—Se(1)—C(10) | 97.92(9) |
| Re(1)—Cl(1) | 2.4797(6) | C(1)—Re(1)—C(2) | 90.31(9) | Re(1)—Se(2)—C(5) | 102.72(7) |
| Se(1)—C(4) | 1.972(2) | Se(1)—Re(1)—C(3) | 97.15(7) | Re(1)—Se(2)—C(20) | 105.42(6) |
| Se(1)—C(10) | 1.929(2) | Se(2)—Re(1)—C(3) | 174.41(6) | C(5)—Se(2)—C(20) | 102.39(9) |
| Se(2)—C(5) | 1.957(2) | C(1)—Re(1)—C(3) | 90.53(9) | Re(1)—C(1)—O(1) | 178.16(9) |
| Se(2)—C(20) | 1.927(2) | C(2)—Re(1)—C(3) | 87.87(9) | Re(1)—C(2)—O(2) | 177.8(2) |
| O(1)—C(1) | 1.158(3) | Se(1)—Re(1)—Cl(1) | 82.92(2) | Re(1)—C(3)—O(3) | 176.4(2) |
| O(2)—C(2) | 1.149(3) | Se(2)—Re(1)—Cl(1) | 80.95(2) | Se(1)—C(4)—C(5) | 111.5(2) |
| O(3)—C(3) | 1.153(3) | C(1)—Re(1)—Cl(1) | 172.25(6) | Se(2)—C(5)—C(4) | 115.4(2) |

TABLE 5

Selected bond distances (Å) and bond angles (°) for $C_{18}H_{16}O_3Cl\,Se_2Re$ (6)

| Bond lengths | | Bond angles | | Bond angles | |
|---|---|---|---|---|---|
| Re(1)—Se(1) | 2.6277(4) | Se(1)—Re(1)—Se(2) | 81.86(12) | C(2)—Re(1)—Cl(1) | 90.91(11) |
| Re(1)—Se(2) | 2.6298(4) | Se(1)—Re(1)—C(1) | 87.67(11) | C(3)—Re(1)—Cl(1) | 90.56(10) |
| Re(1)—C(1) | 1.987(5) | Se(2)—Re(1)—C(1) | 89.10(10) | Re(1)—Se(1)—C(4) | 105.58(12) |
| Re(1)—C(2) | 1.928(4) | Se(1)—Re(1)—C(2) | 174.09(10) | Re(1)—Se(1)—C(10) | 110.23(10) |
| Re(1)—C(3) | 1.928(3) | Se(2)—Re(1)—C(2) | 92.30(10) | C(4)—Se(1)—C(10) | 96.19(16) |
| Re(1)—Cl(1) | 2.4800(9) | C(1)—Re(1)—C(2) | 91.35(15) | Re(1)—Se(2)—C(6) | 106.36(11) |
| Se(1)—C(4) | 1.977(4) | Se(1)—Re(1)—C(3) | 96.62(10) | Re(1)—Se(2)—C(20) | 110.53(10) |
| Se(2)—C(6) | 1.980(4) | Se(2)—Re(1)—C(3) | 178.17(10) | C(6)—Se(2)—C(20) | 94.70(16) |
| Se(1)—C(10) | 1.933(3) | C(1)—Re(1)—C(3) | 89.84(14) | Re(1)—C(1)—O(1) | 176.7(4) |
| Se(2)—C(20) | 1.936(4) | C(2)—Re(1)—C(3) | 89.21(14) | Re(1)—C(2)—O(2) | 179.7(3) |
| O(1)—C(1) | 1.048(6) | Se(1)—Re(1)—Cl(1) | 90.04(2) | Re(1)—C(3)—O(3) | 178.0(3) |
| O(2)—C(2) | 1.151(4) | Se(2)—Re(1)—Cl(1) | 90.44(2) | Se(1)—C(4)—C(5) | 112.2(2) |
| O(3)—C(3) | 1.150(4) | C(1)—Re(1)—Cl(1) | 177.71(12) | Se(2)—C(6)—C(5) | 114.6(3) |

The invention claimed is:

1. A rhenium complex of Formula (I)

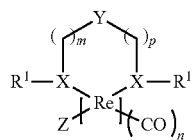
(I)

or a pharmaceutically acceptable salt or a solvate thereof, wherein:

X is Se;

Y is NH, O, or S or is a methylene group;

Z is halogen;

m is 0, 1, or 2, and p is 0, 1, or 2, provided that m and p are both different from zero when Y is NH, O, or S;

n is 3; and $R^1$ is a phenyl group or a group represented by Formula —$(CH_2)_q$—COOH, wherein q is 1 or 2.

2. The rhenium complex as claimed in claim 1, or the pharmaceutically acceptable salt or the solvate thereof, wherein $R^1$ is the group of the Formula —$(CH_2)_q$—COOH, wherein q is 1 or 2.

3. The rhenium complex as claimed in claim 1, or the pharmaceutically acceptable salt or the solvate thereof, wherein:

m and p are 1 and Y is $CH_2$ or NH; or one of m or p is zero and the other is 1 and Y is $CH_2$.

4. The rhenium complex as claimed in claim 1, or the pharmaceutically acceptable salt or the solvate thereof, wherein said complex of the Formula (I) is a complex of Formula (Ia) or Formula (Ib):

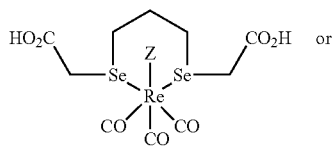
(Ia)
or

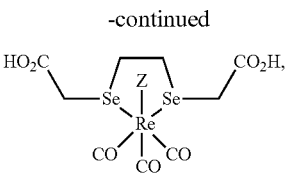
(Ib)

wherein Z is Cl or Br.

5. A pharmaceutical composition comprising a therapeutically effective amount of at least one rhenium complex represented by Formula (I)

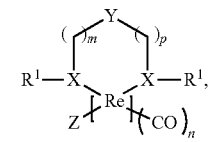
(I)

or a pharmaceutically acceptable salt or a solvate thereof, wherein:

X is selected from the group consisting of Se and Te;

Y is NH, O, or S or is a methylene group;

Z is halogen;

m is 0, 1, or 2 and p is 0, 1, or 2, provided that m and p are both different from zero when Y is NH, O, or S;

n is 3; and $R^1$ is a phenyl group or a group of general Formula —$(CH_2)_q$—COOH, wherein q is 1 or 2.

6. A method for preparing a rhenium complex as claimed in claim 1, comprising a step of reacting a compound represented by Formula (II) with $Re(CO)_5Cl$:

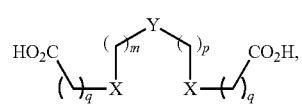
(II)

wherein X, Y, m, p, and q in the Formula (II) are as defined in claim 1 for the compound of the Formula (I).

7. The pharmaceutical composition according to claim 5, further comprising at least one material selected from the group consisting of a pharmaceutically acceptable carrier, a pharmaceutically acceptable vehicle, a pharmaceutically acceptable diluent, and a pharmaceutically acceptable excipient.

8. The pharmaceutical composition according to claim 5, wherein the pharmaceutical composition contains the at least one rhenium complex in an amount that is therapeutically effective on a tumor in a mammal.

9. The pharmaceutical composition according to claim 5, wherein the pharmaceutical composition is in an oral form.

10. A pharmaceutical composition comprising: a therapeutically effective amount of at least one rhenium complex represented by Formula (I); and a therapeutically effective amount of an anti-cancer agent, wherein the at least one rhenium complex of the Formula (I) is

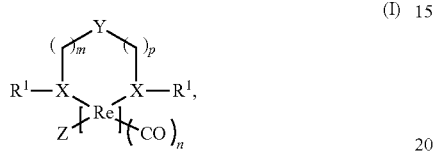

(I)

or a pharmaceutically acceptable salt or a solvate thereof, wherein:

X is selected from the group consisting of S, Se, and Te;
Y is NH, O, or S or is a methylene group;
Z is halogen;
m is 0, 1, or 2 and p is 0, 1, or 2, provided that m and p are both different from zero when Y is NH, O, or S;
n is 3; and
$R^1$ is a phenyl group or a group of general Formula $-(CH_2)_q-COOH$, wherein q is 1 or 2.

* * * * *